(12) United States Patent
Gennadios et al.

(10) Patent No.: US 6,685,961 B1
(45) Date of Patent: Feb. 3, 2004

(54) COLORED GELATIN-BASED FORMULATIONS AND METHOD

(75) Inventors: Aristippos Gennadios, Greensboro, NC (US); Michelle A. Gillette, High Point, NC (US); Roger E. Gordon, Greensboro, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 0 days.

(21) Appl. No.: 09/695,537

(22) Filed: Oct. 24, 2000

(51) Int. Cl.$^7$ .............................. A61K 9/64; A61K 9/48; A61K 47/00; C09B 63/00
(52) U.S. Cl. ...................... 424/456; 424/451; 424/439; 106/402
(58) Field of Search .................. 427/2.17; 426/250; 424/400, 466, 473, 422, 439, 401, 451, 456; 106/402

(56) References Cited

U.S. PATENT DOCUMENTS

| | | | |
|---|---|---|---|
| 2,431,001 A | 11/1947 | Sullivan | 117/76 |
| 3,231,592 A | 1/1966 | McCord | 260/414 |
| 3,483,002 A | 12/1969 | Stein | 99/148 |
| 3,677,691 A | 7/1972 | Koch | 8/41 |
| 3,976,797 A | 8/1976 | Furia | 426/131 |
| 4,167,422 A | 9/1979 | Bellanca et al. | 106/289 |
| 4,263,333 A | 4/1981 | Maing et al. | 426/540 |
| 4,500,453 A | 2/1985 | Shank | 260/117 |
| 4,773,936 A * | 9/1988 | Clark et al. | |
| 5,260,073 A | 11/1993 | Phipps | 424/465 |
| 5,279,655 A | 1/1994 | Takazawa et al. | 106/22 D |
| 5,288,316 A | 2/1994 | Auslander et al. | 106/27 R |
| 5,340,582 A | 8/1994 | Sugasawa et al. | 424/401 |
| 5,405,642 A | 4/1995 | Gilis et al. | 427/2.23 |
| 5,417,990 A | 5/1995 | Soedjak et al. | 426/89 |
| 5,490,994 A | 2/1996 | Soedjak | 426/262 |
| 5,558,880 A * | 9/1996 | Gole et al. | 424/484 |
| 5,609,992 A | 3/1997 | Sorori et al. | 430/281.1 |
| 5,874,106 A | 2/1999 | Adesunloye et al. | 424/456 |
| 6,027,739 A | 2/2000 | Nichols | 424/401 |

FOREIGN PATENT DOCUMENTS

| | | |
|---|---|---|
| EP | 0092908 | 11/1983 |
| WO | WO 0132036 | 5/2001 |

OTHER PUBLICATIONS

Digenis, G.A., et al.; "Cross–Linking of Gelatin Capsules and Its Relevance to Their in Vitro–In Vivo Performance"; Journal of Pharmaceutical Sciences; vol. 83, No. 7, pp. 915–921; Jul. 1994.

* cited by examiner

*Primary Examiner*—Thurman K. Page
*Assistant Examiner*—Humera N. Sheikh
(74) *Attorney, Agent, or Firm*—Womble, Carlyle Sandridge & Rice, PLLC

(57) ABSTRACT

The present invention is a process for coloring gelatin-based formulations involving adding a saturated fatty acid to the gelatin-based formulation along with lake pigment, whereby the saturated fatty acid is added in an amount so as to prevent cross-linking between the gelatin-based formulations and the aluminum cations released by the lake pigments. Preferably, this amount is about 10% to about 300% by weight of the added lake pigment content. With this process, the resulting colored gelatin exhibits acceptable machineability characteristics and disintegration. As an example, the colored gelatin produced by this process has a viscosity of less than approximately 10,000 cP at about 60° C. Additionally, the present invention is a gelatin-based formulation made from the above-described process. The gelatin-based formulation includes gelatin, lake pigment(s), and a sufficient amount of fatty acid to prevent cross-linking between the gelatin and the cations released from the lake pigment(s). Further, the present invention includes a dosage form that includes the described gelatin-based formulation as the sheath material. The dosage form may encapsulate a liquid, suspension, semi-solid, or solid pharmaceutical, nutritional, herbal, or personal care product, or combination thereof.

31 Claims, No Drawings

COLORED GELATIN-BASED FORMULATIONS AND METHOD

FIELD OF THE INVENTION

The present invention relates generally to a process for coloring gelatin-based formulations and specifically to a process for preventing the cross-linking between gelatin and the aluminum cations of lake pigments through incorporation of fatty acids.

BACKGROUND OF THE INVENTION

Gelatin, a collagen-derived protein, is used in a variety of commercial products. For example, gelatin capsules generally are comprised of a gelatin sheath encapsulating a fill of pharmaceutical, nutritional, herbal, or personal care products. The fill may be a liquid, suspension, solid, or semi-solid. For example, see commonly-owned U.S. Pat. Nos. 5,146,730 and 5,459,983, each herein incorporated in their entirety, as examples of using gelatin for enrobing solid products. As another example, for soft gelatin capsules or tablets, the gelatin sheath or shell includes a plasticizer, normally glycerin or sorbitol, to control the softness and flexibility of the sheath. The sheath also includes water, and optionally, other additives, such as flavorants or colorants. Gelatin is used for hard shell encapsulation and dipped products as well. Gelatin is also recognized for use in a variety of food products. For example, soups, canned meats and vegetables, jams, jellies, ice cream, marshmallows, and confectionery items may include a gelatin constituent.

Gelatin formulations (gel masses) may be colored using a variety of water-soluble FD&C and D&C dyes and exempt colorants. In production of multi-tone gelatin capsules (or gelatin-coated cores), the water-soluble dyes tend to bleed, smear, or otherwise become tarnished from the darker ("stronger") color to the lighter ("weaker") color. Such bleeding particularly occurs across any seam that exists on the gelatin capsule or gelatin-coated core. Similar bleeding problems occur with other gelatin products, as well. Due to the problems associated with certified water-soluble dyes and exempt colorants, lake pigments present a water-insoluble substitute. Lake pigments are known in the art of colorants for edible products. Lake pigments are aluminum or calcium salts of water-soluble FD&C or D&C dyes or exempt colorants, like carmine. The water-soluble dyes and colorants are rendered water insoluble through absorption onto an alumina hydrate substrate. Due to the insolubility of lake pigments in water, the lake pigments color by dispersion. The water-insolubility of lake pigments provides a solution to the aforementioned problems associated with bleeding, smearing, or marking across strong to weak colors.

The use of lake pigments, however, presents other potential negative effects. During manufacturing of gelatin-based formulations and conditioning on heat, aluminum cations ($Al^{+3}$) are released from the lake pigments. The cations interact (cross-link) with the gelatin causing the gelatin to become thick and tough. Specifically, with respect to gelatin-based capsule manufacture, cross-linked gelatin is unmachineable, i.e., difficult to process on an encapsulating machine. The interaction between the cations and the negatively charged sites along gelatin molecules results in the deleterious cross-linking. The cross-linked gelatin is highly viscous and tough, and for example, the cross-linked tough masses are difficult to cut using the rotary die encapsulation machines known in the art of gelatin capsule manufacture. Further, resulting dried gelatin shells produced from the cross-linked gelatin can exhibit unacceptable delayed disintegration.

U.S. Pat. No. 4,500,453 to Shank discloses cross-linked collagen-derived protein compositions as having increased strength and viscosity. Gelatin is specifically reacted with aluminum salts of acetic acid in order to increase the viscosity of the protein. While the '453 patent presents such cross-linking (and the associated increase in viscosity) as beneficial, the present inventors, in fact, seek to prevent such interaction as undesirable due to the highly viscous nature and other resulting deleterious properties of the cross-linked protein product.

The extent to which the aluminum cations release from the lake pigments depends on the particular lake pigment. For example, the present inventors have noted that FD&C Red #40 lake exhibits a greater tendency for aluminum cation release. In turn, therefore, when FD&C Red #40 lake is used to color gelatin-based formulations, the resulting colored gelatin-based formulations often are thick and unmachineable.

One solution to the cross-linking problem has been to add a chelating agent, such as ethylenediaminetetraacetic acid (EDTA). The chelating agent approach, however, has been only partially successful in preventing cross-linking. The costs for such agents, as well, prevent this approach from being a preferable solution.

There is a need therefore, for an economical process for coloring gelatin-based formulations with lake pigments that effectively prevents the undesirable cross-linking that occurs between the gelatin-based formulations and the aluminum cations.

SUMMARY OF THE INVENTION

The present invention is a process for coloring gelatin-based formulations involving adding a saturated fatty acid to the gelatin along with powdered or granular lake pigment or lake pigment pre-dispersed in glycerin, whereby the saturated fatty acid is added in an amount so as to prevent cross-linking between the gelatin and the aluminum cations released by the lake pigments. Preferably, this amount is about 10% to about 300% by weight of the added lake pigment content. With this process, the resulting colored gelatin-based formulations exhibit acceptable machineability characteristics and disintegration. As an example, the colored gelatin formulation produced by this process has a viscosity of less than approximately 10,000 centipoise (cP) at 60° C. Also, specimens (1.5 cm width×1.5 cm length×1.0 cm height) of gelatin-based formulations solidified at ambient temperature disintegrated completely in water (37° C.) using standard laboratory disintegration equipment (with a cylindrical disc) within approximately 25 minutes.

Additionally, the present invention is a gelatin-based formulation made from the above-described process. The gelatin-based formulation includes gelatin, lake pigment(s), and a sufficient amount of fatty acid to prevent cross-linking between the gelatin and the cations released from the lake pigment(s). Further, the present invention includes a dosage form that includes the described gelatin-based formulation as the sheath material. The dosage form may encapsulate a liquid, suspension, semi-solid, or solid pharmaceutical, nutritional, herbal, or personal care product, or combination thereof.

These and other aspects of the present invention as disclosed herein will become apparent to those skilled in the art after a reading of the following description of the preferred embodiments.

DETAILED DESCRIPTION OF THE PREFERRED EMBODIMENT

The present invention is directed to a process for coloring gelatin-based formulations. As used herein, the term "gelatin" should be considered to include other polymeric substances, either natural or synthetic, that have negative charges capable of interaction with cations, such as the aluminum cations released by lake pigments. Preferably, the present invention is a process for producing colored gelatin-based formulations suitable for use as a gelatin sheath encapsulating a medicament in a liquid, suspension, solid or semi-solid. However, the invention is applicable to coloring gelatin-based formulations in general.

The preferred gelatin-based capsule sheath composition is characterized by flexibility and a non-tacky consistency. These desired physical characteristics are based upon the formation of capsules using encapsulation machinery. While the gelatin-based formulation must be flexible for machineability, the gelatin-based formulation must also exhibit appropriate integrity to enclose a liquid, suspension, paste, or solid fill material for an extended period of time, e.g., up to about two years, without leakage. Also, the gelatin-based formulation must be soluble upon consumption.

One form of gelatin capsule production known in the art uses a rotary die process in which a molten mass of a gelatin-based sheath formulation is fed from a reservoir onto cooled drums to form two spaced sheets or ribbons of the gelatin-based formulation in a semi-molten state. These ribbons are fed around rollers and brought together at a convergent angle into the nip of a pair of roller dies that include opposed die cavities. The material to be encapsulated is fed into the wedge-shaped joinder of the ribbons. The gelatin ribbons are continuously conveyed between the dies, with portions of the medicament being trapped between the sheets inside the die cavities. The sheets are then pressed together, and severed around each die so that opposed edges of the sheets flow together to form a continuous gelatin-based sheath around the entrapped medicament. The part of the gelatin-based sheath that is severed from the segments forming the capsules is then collected and discarded or recycled. The soft capsules are then dried to increase the integrity of the sheath, and packaged for later distribution and consumption. Other encapsulating machines are equally applicable for gelatin-based formulations prepared using the present invention, such as that disclosed in U.S. Pat. Nos. 5,146,730 and 5,549,983, previously incorporated by reference hereto, and also hard shell capsules and tablets, and gelatin-dipped products as well.

Manufacture of uniform soft gelatin capsules requires a sheath material that has good "machineability," i.e., it is important that the sheath material be of a non-tacky or non-sticky nature, so that the sheath material can be brought into contact with the rollers without sticking. Further, if the gelatin-based formulation is highly viscous, "thick," and/or tough, it will also affect the machineability of the gelatin sheath material on the encapsulating machine.

The present invention is a process for coloring gelatin-based formulations without sacrificing the machineability of the resulting colored gelatin-based formulations. The process includes adding fatty acids to the gelatin-based formulation in an amount sufficient to prevent cross-linking between the gelatin and the lake pigments. The present inventors propose that fatty acids incorporated into the gelatin mass complex the aluminum cations thereby preventing their reaction with the gelatin. Other phenomena, however, may be applicable and the above theory should not be used to limit the scope of the present invention. Minor amounts of fatty acids have been used in gelatin-coated capsule, caplet, or tablet manufacture to provide slippage of the gelatin away from the die of the encapsulation machine. As described in more detail below, however, the present invention presents a novel use of fatty acids in sufficient amounts so as to adequately complex aluminum cations released from lake pigments.

Although either saturated or unsaturated fatty acids may be used, saturated fatty acids are preferred as more effective at complexing the aluminum cations. Examples of preferred saturated fatty acids are stearic acid, palmitic acid, lauric acid, and myristic acid, and combinations thereof. One particularly preferred fatty acid product contains a minimum content of 40% by weight stearic acid and a minimum content of 40% by weight of palmitic acid. Stauber Performance Ingredients, Inc. of Brea, Calif. distributes such a product under the trade name TRISTAR 149. Any appropriate fatty acid, however, may be used.

Preferably, the fatty acid is added in an amount of about 10% to about 300% by weight of the added lake pigment content. More preferably, the fatty acid is added in an amount of about 80% to about 150% by weight of the added lake pigment content. More preferably, the fatty acid is added in an amount above about 85% by weight of the added lake pigment.

Any acceptable method of producing gelatin-based formulations may incorporate the present invention, and the following examples merely illustrate particular embodiments thereof. Thus, the below examples are for the purpose of describing a preferred embodiment of the invention and are not intended to limit the present invention.

EXAMPLE 1

Dispersions of lake pigment and titanium dioxide ($TiO_2$) were added to gelatin-based preparations comprised of about 45% gelatin, about 9% glycerin (plasticizer), and about 46% purified water (see, e.g., preparations described in commonly-owned U.S. Pat. Nos. 5,146,730 and 5,459,983). The gelatin used was pharmaceutical grade limed bone (Type B) gelatin having a Bloom strength of 150. One preferred lake pigment dispersion contains 20% FD&C Red #40 powdered lake pigment in 80% glycerin and one preferred $TiO_2$ dispersion contains 66.67% glycerin and 33.33% $TiO_2$ powder. Prior to adding the colorant, the gel mass preparations were cooked in a 70° C. water bath for approximately two (2) hours. After addition of the colorant, the mixture was aged in a 60° C. water bath for 24 hours.

Preferably, the fatty acids are added to the gel mass preparation prior to the addition of the lake pigments. Thus, prior to adding the colorant, powdered fatty acid, e.g., the stearic acid/palmitic acid mixture described hereinabove, was added. Alternatively, the fatty acid may be melted by heating it in small amounts of water and then added to the gel mass preparation. After 24 hours of gel aging, the resulting colored gels were sampled to determine their viscosity. Then, the colored gels were allowed to solidify ("set") at ambient temperature and the disintegration times of solid gel specimens were determined.

Gel viscosity was determined at 60° C. using a Brookfield DV-II+ viscometer under standard operating procedures. For proper capsule, caplet, or tablet machineability, gel mass preparations should have a viscosity between about 5,000 cP and about 30,000 cP at 60° C. Preferably, the resulting colored gel mass has a viscosity of less than approximately 15,000 cP at 60° C. More preferably, the gel mass exhibits a viscosity of between about 7,500 and 10,000 cP at 60° C.

Gel disintegration times were determined on gel specimens (1.5 cm width×1.5 cm length×1.0 cm height) cut from solidified gel masses that were allowed to solidify ("set") at ambient temperature. The pieces (or specimens) were disintegrated in water at 37° C. with an analytical lab disintegration apparatus having a cylindrical disc used for capsule disintegration testing as described in *United States Pharmacopoeia/National Formulary*. More specifically, a QC-21 Disintegration Test System from Hanson Research (Chatsworth, Calif.) was used. Without regard to enteric coatings, the gel preferably should disintegrate within approximately 50 minutes. More preferably, the resulting colored gelatin-based formulations disintegrate in less than approximately 40 minutes. More preferably, the disintegration time is approximately 25 minutes or less.

TABLE 1

| Sample Fatty Acid Content (% By Weight Dry Pigment) | Viscosity (cP) | Disintegration (Min:Sec) |
|---|---|---|
| 84.175% | 13,360 | 27:10 |
| 100% | 12,300 | 25:00 |
| 125% | 9,960 | 23:05 |
| 150% | 8,970 | 20:35 |

As stated above, a possible prior method to solve the cross-linking problem was to add a chelating agent such as EDTA. The present invention may be used in conjunction with EDTA as well. The resulting gelatin-based formulation formed using the EDTA/fatty acid mixture is more machineable than the gelatin would be using the EDTA alone. The following table represents several examples of an EDTA/fatty acid mixture and the resulting viscosity values and disintegration times.

TABLE 2

| Sample (% By Weight Dry Pigment) | Viscosity (cP) | Disintegration (Min:Sec) |
|---|---|---|
| 2.5%EDTA 0% fatty acid | 77,120 | 69:20 |
| 50% EDTA 0% fatty acid | 44,600 | 48:05 |
| 2.5% EDTA 84.175% fatty acid | 14,990 | 40:05 |
| 10% EDTA 84.175% fatty acid | 15,010 | 36:10 |
| 2.5% EDTA 150% fatty acid | 8,870 | 32:10 |

As demonstrated by the above tables, the present invention provides an improved colored gelatin-based formulation. For example, in comparing the viscosity values and disintegration times of the colored gelatin-based formulation featured in the last row of each table (i.e. each having 150% fatty acid content by weight of dry lake content), the gel having no EDTA performs just as well or better than the gel containing the addition of 2.5% EDTA. Thus, the fatty acids appear to be more effective than the EDTA at complexing the aluminum cations.

The scope of the present invention should be interpreted to include the colored gelatin-based product formed by the above-described process of adding fatty acids in a sufficient amount to prevent cross-linking between the gelatin-based formulation and the released aluminum cations from the lake pigments.

EXAMPLE 2

As a further example of the effectiveness of fatty acids to complex metal cations, aluminum acetate was added at 5 g/kg of a gel mass prepared with 150 Bloom limed bone (Type B) gelatin. Prior to adding the aluminum acetate, the gel mass preparations were cooked in a 70° C. water bath for approximately two (2) hours. After addition, the mixture was aged in a 60° C. water bath for 24 hours.

Similar to Example 1, preferably fatty acids were added to the gel mass preparation prior to the addition of the aluminum acetate. As stated above, alternative methods for adding the fatty acid(s) are available. Gel viscosity and disintegration times were determined -based upon the methods discussed hereinabove for Example 1. A variety of fatty acids and combinations of fatty acids were evaluated, as shown by Table 3 below. Again, EDTA was also used to demonstrate the comparative effectiveness of the present invention.

TABLE 3

| Complexing Agent Evaluated | Complexing Agent Content (per kg of gel) | Viscosity (cP) | Disintegration (Min:Sec) |
|---|---|---|---|
| Lauric Acid | 2.5 g/kg | 7030 | 31:50 |
| Lauric Acid | 7.5 g/kg | 6310 | 23:33 |
| Myristic Acid | 2.5 g/kg | 6900 | 26:00 |
| Myristic Acid | 7.5 g/kg | 6430 | 30:17 |
| Stearic-Palmitic Acid | 2.5 g/kg | 7940 | 21:67 |
| Stearic-Palmitic Acid | 7.5 g/kg | 6510 | 24:28 |
| EDTA | 2.5 g/kg | 36060 | 57:28 |
| EDTA | 7.5 g/kg | 6940 | 24:61 |

As demonstrated, the present invention provides an improved, more machineable gel mass preparation. Thus, regardless of the source of the metal cations, the present invention provides an economical solution for alleviating the problems associated with undesirable cross-linking between those cations and gelatin-based formulations.

Although specific embodiments of the present invention have been illustrated and described in detail, it is to be expressly understood that the invention is not limited thereto. The above detailed description of the embodiment is provided for example only and should not be construed as constituting any limitation of the invention. For example, those skilled in the art will recognize that the present invention will apply to complexing divalent or trivalent cations, other than aluminum cations, such as iron, calcium, or magnesium cations, as well. Thus, modifications will be obvious to those skilled in the art, and all modifications that do not depart from the spirit of the invention are intended to be included within the scope of the appended claims.

What is claimed is:

1. A process for coloring gelatin-based formulations comprising:
    adding lake pigment to the gelatin-based formulations; and
    adding fatty acids to the gelatin-based formulation in an amount sufficient to prevent cross-linking between the gelatin and the lake pigments.

2. The process of claim 1 wherein the fatty acid is saturated.

3. The process of claim 1 wherein the fatty acid is selected from the group consisting of stearic, palmitic, lauric, myristic, and combinations thereof.

4. The process of claim 1 wherein the fatty acid is added in an amount of about 10% to about 300% by weight of the added lake pigment content.

5. The process of claim 1 wherein the fatty acid is added in an amount of about 80% to about 150% by weight of the added lake pigment content.

6. The process of claim 1 wherein the fatty acids are added to the gelatin-based formulations prior to the addition of the lake pigments.

7. The process of claim 1 wherein the resulting colored gelatin-based formulation has a viscosity in the range of about 5,000 cP to about 30,000 cP at about 60° C.

8. The process of claim 1 wherein the resulting colored gelatin-based formulation has a viscosity less than about 15,000 cP at about 60° C.

9. The process of claim 1 wherein the resulting colored gelatin-based formulation has a viscosity between about 7,500 cP and about 10,000 cP at about 60° C.

10. The process of claim 1 wherein the resulting colored gelatin-based formulation exhibits an acceptable rate of disintegration.

11. The process of claim 1 wherein the lake pigment is FD&C Red #40 Lake.

12. The product formed by the process of claim 1.

13. A process for coloring gelatin-based formulations comprising:
    adding a saturated fatty acid to the gelatin-based formulation; and
    adding lake pigment to the gelatin-based formulation,
    whereby the saturated fatty acid is added in an amount of about 10% to about 300% by weight of the added lake pigment content so as to prevent cross-linking between the gelatin-based formulation and the lake pigments and provide a resulting colored gelatin-based formulation having a viscosity of less than approximately 15,000 cP at about 60° C.

14. The product formed by the process of claim 13.

15. A gelatin-based formulation comprising:
    gelatin;
    lake pigment in an amount sufficient to color the gelatin; and
    fatty acid in an amount sufficient to prevent cross-linking between the gelatin and the lake pigment.

16. The gelatin-based formulation according to claim 15 wherein the fatty acid is selected from the group consisting of stearic, palmitic, lauric, myristic, and combinations thereof.

17. The gelatin-based formulation according to claim 15 wherein the fatty acid is added in an amount of about 10% to about 300% by weight of the lake pigment content.

18. The gelatin-based formulation according to claim 15 wherein the fatty acid is added in an amount of about 80% to about 150% by weight of the lake pigment content.

19. A dosage form comprising:
    (a) a fill; and
    (b) a gelatin-based sheath comprising:
        gelatin;
        lake pigment in an amount sufficient to color the gelatin; and
        fatty acid in an amount sufficient to prevent cross-linking between the gelatin and the lake pigment.

20. The dosage form according to claim 19 wherein the fill is a liquid, suspension, semi-solid, or solid.

21. The dosage form according to claim 19 wherein the fill is a pharmaceutical, nutritional, herbal, or personal care product.

22. The dosage form according to claim 19 wherein the fatty acid is selected from the group consisting of stearic, palmitic, lauric, myristic, and combinations thereof.

23. The dosage form according to claim 19 wherein the fatty acid is added in an amount of about 10% to about 300% by weight of the added lake pigment content.

24. The dosage form according to claim 19 wherein the fatty acid is added in an amount of about 80% to about 150% by weight of the added lake pigment content.

25. A process for treating gelatin-based formulations comprising:
    adding a source of metal cations to the gelatin-based formulation; and
    adding fatty acids to the gelatin in an amount sufficient to prevent cross-linking between the gelatin and the cations.

26. The process of claim 25 wherein the source of metal cations is a lake pigment.

27. The process of claim 25 wherein the fatty acid is selected from the group consisting of stearic, palmitic, lauric, myristic, and combinations thereof.

28. The process of claim 25 wherein the fatty acid is added in an amount of about 10% to about 300% by weight of the added lake pigment content.

29. The process of claim 25 wherein the fatty acid is added in an amount of about 80% to about 150% by weight of the added lake pigment content.

30. The process of claim 25 wherein the resulting colored gelatin-based formulation has a viscosity less than about 15,000 cP at about 60° C.

31. The product formed by the process of claim 25.

* * * * *